US009440906B2

(12) United States Patent
Ogbourne

(10) Patent No.: US 9,440,906 B2
(45) Date of Patent: *Sep. 13, 2016

(54) CRYSTALLINE INGENOL MEBUTATE

(71) Applicant: LEO Laboratories Limited, Dublin (IE)

(72) Inventor: Steven Martin Ogbourne, Pinbarren (AU)

(73) Assignee: LEO Laboratories Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/182,274

(22) Filed: Feb. 17, 2014

(65) Prior Publication Data

US 2015/0025265 A1    Jan. 22, 2015

Related U.S. Application Data

(63) Continuation of application No. 13/088,910, filed on Apr. 18, 2011, now Pat. No. 8,653,133.

(60) Provisional application No. 61/325,032, filed on Apr. 16, 2010.

(51) Int. Cl.
  C07C 67/52      (2006.01)
  C07C 69/533     (2006.01)
  A61K 9/00       (2006.01)
  A61K 9/06       (2006.01)

(52) U.S. Cl.
  CPC ............ C07C 67/52 (2013.01); C07C 69/533 (2013.01); *A61K 9/0014* (2013.01); *A61K 9/0034* (2013.01); *A61K 9/06* (2013.01); *C07B 2200/13* (2013.01); *C07C 2103/86* (2013.01)

(58) Field of Classification Search
  None
  See application file for complete search history.

(56) References Cited

FOREIGN PATENT DOCUMENTS

| EP | 1015413 A1 | 7/2000 |
|----|------------|--------|
| WO | WO2007/059584 | * 5/2007 |
| WO | WO-2007053912 A1 | 5/2007 |
| WO | WO-2007059584 A1 | 5/2007 |
| WO | WO-2007068963 A2 | 6/2007 |
| WO | WO-2008131491 A1 | 11/2008 |
| WO | WO-2011128780 A1 | 10/2011 |

OTHER PUBLICATIONS

Florence et al. (Natural products isolation, 2nd ed., 2006, Human Press Inc., Chapter 11, p. 275-295).*
Adolf et al., *3-O-angeloylingenol, The Toxic and Skin Irritant Factor from Latex of Euphorbia anitiquorum L. (Euphorbiaceae) and from a Derived Thai Purgative and Anthelimintic (Vermifuqe) Drug*, J. Science. Soc. Thailand, 9:81-88 (1983).
Hohmann et al., *Diterpenoids from Euphorbia peplus*, Planta Med., 9:291-294 (2000).
Marco et al., *Ingenane and lathyrane diterpenes from the latex of Euphorbia canariensis*, Phytochemistry, 45(3):563-570 (Jun. 1, 1997).
Ogbourne et al., *Proceedings of the First International Conference on PEP005*, Anti-Cancer Drugs, 18(3):357-362 (Mar. 1, 2007).

* cited by examiner

*Primary Examiner* — Bong-Sook Baek
(74) *Attorney, Agent, or Firm* — Fish & Richardson P.C.

(57) ABSTRACT

The present invention relates to a novel crystalline form of ingenol mebutate, methods of preparation thereof, and to its use. More specifically, the invention relates to the conversion of amorphous ingenol mebutate (ingenol-3-angelate, PEP005) to a crystalline form, which was characterized by single crystal X-Ray crystallography (XRC), attenuated total reflectance Fourier transform infrared (FTIR-ATR) spectroscopy and Differential Scanning calorimetry (DSC).

16 Claims, 1 Drawing Sheet

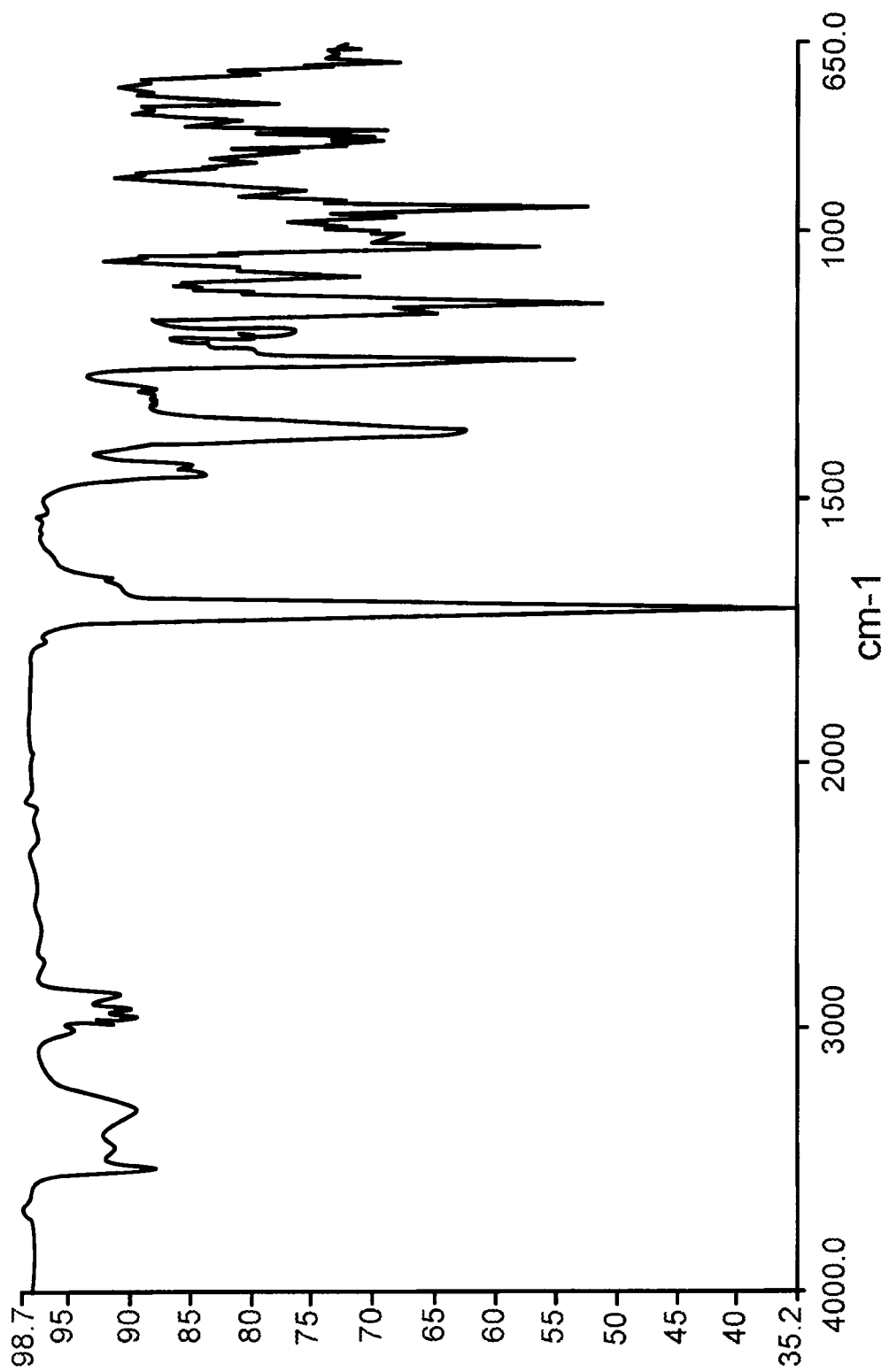

CRYSTALLINE INGENOL MEBUTATE

CROSS-REFERENCE TO RELATED APPLICATIONS

This application is a continuation of U.S. patent application Ser. No. 13/088,910, filed Apr. 18, 2011, allowed, which claims the benefit of and priority to U.S. Provisional patent application No. 61/325,032, filed Apr. 16, 2010. The contents of each of the foregoing applications are incorporated herein by reference.

FIELD OF THE INVENTION

This invention relates to a novel crystalline form of ingenol mebutate, methods of preparation thereof, and to its use.

BACKGROUND OF THE INVENTION

Ingenol mebutate has the structure shown in Formula 1 and the following chemical names:
1) 2-Butenoic acid, 2-methyl (1aR,2S,5R,5aS,6S,8aS,9R,10aR)-1a,2,5,5a,6,9,10,10a-octahydro-5,5a-dihydroxy-4-(hydroxymethyl)-1,1,7,9-tetramethyl-11-oxo-1H-2,8a-methanocyclopenta[a]cyclopropa[e]cyclodecen-6-yl ester, (2Z)—
2) (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H2,8a-methanocyclopenta[a]cyclopropa[e]cyclodecen-6-yl(2Z)-2-methylbut-2-enoate)

Formula 1

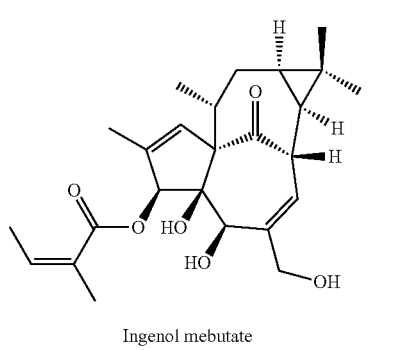

Ingenol mebutate

Ingenol mebutate (synonyms: PEP005, ingenol-3-angelate, CAS no. 75567-37-2) can be isolated from various *Euphorbia* species, and particularly from *Euphorbia peplus* and *Euphorbia drummondii*. Ingenol mebutate has the structure shown in Formula 1.

The preparation of Ingenol mebutate by extraction with 95% ethanol from the sap of *Euphorbia peplus*, *Euphorbia hirta* and/or *Euphorbia drummondi*; followed by chromatographic purification has been disclosed in EP1015413 B1, which is incorporated herein by reference in its entirety. Isolation from *Euphorbia peplus* has also been described by Hohmann et. al. Planta Med. 66, 3, (2000), which is incorporated herein by reference in its entirety. Other patent applications directed to ingenol mebutate and other pharmaceutically active ingenol derivatives include WO 2008/131491, WO 2007/068963, WO 2007/059584 and WO 2007/053912, each of which is incorporated herein by reference in its entirety.

Ingenol mebutate has been found to be highly toxic for skin cancer cells via rapid mitochondrial disruption and cell death by primary necrosis, whereas normal cells are less sensitive to ingenol mebutate.

Ingenol mebutate has been shown to be a potent anti-cancer drug and therapeutically effective in microgram quantities. Recent findings from a Phase III study evaluating ingenol mebutate in the treatment of actinic keratosis (AK), a common pre-cursor to skin cancer, were presented at the 68th Annual Meeting of the American Academy of Dermatology (AAD) (Scientific Session Poster Discussion: P105). Results from REGION-I of the study demonstrated that treatment with ingenol mebutate Gel once daily for 2 consecutive days (n=117) on non-head locations resulted in significant clearance of AK lesions when compared with the vehicle or placebo (n=118). The study showed a median reduction of about 66.7% in the number of AK lesions, ($p<0.0001$), a complete clearance rate of about 27.4% ($p<0.0001$) including on the extremely difficult-to-treat back of hand and arm locations, and a partial clearance rate of about 44.4% ($p<0.0001$).

Ingenol mebutate is commercially available in amorphous form, i.e., from Sigma-Aldrich. However, no crystalline form of ingenol mebuate has been reported.

SUMMARY OF THE INVENTION

This invention is directed to a novel crystalline form of ingenol mebutate, to pharmaceutical compositions comprising this crystalline form, and to methods of its preparation and use.

A first embodiment of the invention thus encompasses a crystalline form of a compound of Formula 1.

In one embodiment, the crystalline form of the compound of Formula 1 has an attenuated total reflectance fourier transform infrared (FTIR-ATR) spectrum essentially similar as shown in FIG. 1:

In another embodiment, a crystalline form of the compound of Formula 1 is characterized by an attenuated total reflectance fourier transform infrared (FTIR-ATR) spectrum exhibiting one or more attenuated total reflectance peaks at approximately 3535, 2951, 1712, 1456, 1378, 1246, 1133, 1028 and/or 956 cm$^{-1}$ (±3 cm$^{-1}$), respectively.

In yet another embodiment, a crystalline form of the compound of Formula 1 has a differential scanning calorimetry (DSC) curve comprising an event with an onset at about 153° C. (±5° C.). The characteristic DSC curve was characterized using a Perkin Elmer DSC 8500, with a heating rate of 20° C./min.

In yet another embodiment, a crystalline form of the compound of Formula 1 has one or more single crystal parameters being listed in Table 1:

TABLE 1

| Crystal Parameters | |
|---|---|
| Crystal system | Orthorhombic |
| Space Group: | $P2_12_12_1$ |
| Unit Cell Dimensions: | a = 7.1295(4) Å |
| | b = 7.7558(4) Å |
| | c = 41.375(2) Å |
| Volume: | 2287.9(2) Å$^3$ |
| Molecules per Unit Cell (Z) | 4 |
| Density (calculated) | 1.250 Mg/m$^3$ |

In yet another embodiment, a crystalline form of the compound of Formula 1 comprises atoms at atomic positions relative to the origin of the unit cell as set forth below in Table 2, or bond lengths or bond angles as set forth below in Table 3.

In yet another embodiment, a crystalline form of the compound of Formula 1 has a structure obtained by single crystal X-Ray crystallography (XRC) as shown in Formula 2:

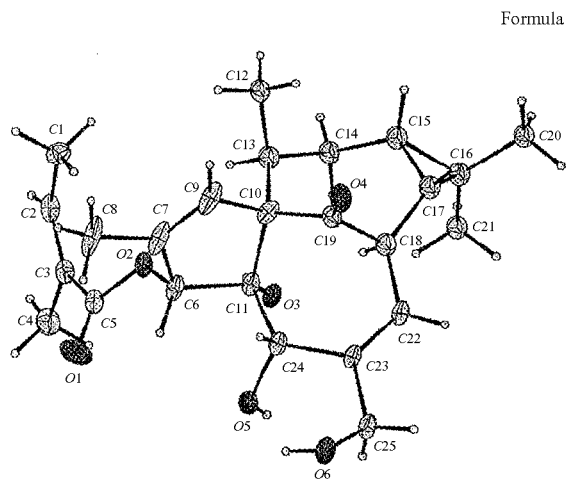

Formula 2

Configuration of crystalline ingenol mebutate
Obtained by single crystal X-Ray crystallography (XRC).
Thermal ellipsoids drawn at the 35% probability level.

In certain embodiments, the invention provides crystalline ingenol mebutate. In certain embodiments, the crystalline form is not a solvate. In certain embodiments, a crystalline form is orthorhombic. In certain embodiments, a crystalline form is further characterized by an FTIR-ATR spectrum exhibiting attenuated total reflectance peaks at approximately 3535, 2951, 1712, 1456, 1378, 1246, 1133, 1028 and/or 956 cm$^{-1}$ (±3 cm$^{-1}$). In certain embodiments, a crystalline form has a differential scanning calorimetry curve comprising an event with an onset at about 153±about 5° C. In certain embodiments, a crystalline form is obtainable by crystallization of the compound of formula 1 from acetone, acetonitrile, ethanol, 2-propanol, heptane, methyl tert-butyl ether, monoglyme, toluene, a mixture of acetone and heptane, a mixture of acetone and c-hexane, a mixture of acetone and i-octane, a mixture of acetone and xylene, a mixture of acetonitrile and water, a mixture of ethanol and water, a mixture of 2-propanol and water, a mixture of 2 propanol and heptane, a mixture of 1,4-dioxane and heptane, a mixture of 1,4-dioxane, dimethyl sulfoxide and heptane or a mixture of toluene and heptane. In embodiments of the invention crystalline ingenol mebutate are obtained from acetonitrile or from a mixture of ethanol and water. In certain embodiments, a crystalline form has XRC single crystal parameters that are substantially identical to those provided in Table 1. In certain embodiments, a crystalline form comprises atoms at atomic positions relative to the origin of the unit cell as set forth in Table 2, or bond lengths or bond angles as set forth in Table 3.

Preferably, a crystalline ingenol mebutate of the present invention has a crystalline purity of at least about 99.5% (e.g., as measured by HPLC as descried in Example 1). In certain embodiments, the crystalline purity is at least about 99.7% or more preferably about 99.72%. In certain embodiments, the crystalline purity is at least about 99.9%.

The invention also provides crystalline ingenol mebutate or highly pure crystalline ingenol mebutate for use as a medicament. The present invention also contemplates the use of crystalline ingenol mebutate or highly pure crystalline ingenol mebutate for the topical treatment of skin disorders, namely, cancers or other skin conditions involving neoplastic cells, such as solar keratosis or actinic keratosis. The skin cancers contemplated by the present invention include, amongst others, skin cancer, melanoma, malignant melanoma, merkel cell carcinoma, squamous cell carcinoma, and basal cell carcinoma (BCC), including superficial-basal cell carcinoma (sBCC).

The invention also provides a pharmaceutical composition comprising crystalline ingenol mebutate or highly pure ingenol mebutate, and one or more pharmaceutically acceptable carriers or vehicles. In certain embodiments, the pharmaceutical composition is suitable for topical administration of a pharmaceutical composition to deliver an effective amount of crystalline ingenol mebutate to a treatment area of the skin to treat a skin disorder. In accordance with the present invention, the pharmaceutical composition can be formulated as a liquid or semi-solid, such as a gel, cream, ointment, salve, balm, liquid, suspension or lotion. The invention also provides a method of making a pharmaceutical composition comprising crystalline ingenol mebutate, the method comprising combining crystalline ingenol mebutate with a pharmaceutically acceptable carrier or vehicle.

The present invention also provides a method of treating a skin disorders, such as cancer or other condition involving neoplastic cells, the method comprising applying an effective amount of a pharmaceutical composition of the invention to a treatment area on a subject in need thereof.

DEFINITIONS

The term "$C_1$-$C_6$ linear or branched alkyl alcohols" includes methanol, ethanol, 1-propanol, 2-propanol, 1-butanol, tert-butanol, and 2-butanol.

The term "$C_2$-$C_6$ linear or branched alkyl nitriles" includes acetonitrile and propionitrile.

BRIEF DESCRIPTION OF THE DRAWINGS

FIG. 1 is a characteristic FTIR-ATR spectrum of crystalline ingenol mebutate, acquired using the Universal Attenuated Total Reflectance accessary on a Perkin Elmer Spectrum One FTIR spectrometer.

DETAILED DESCRIPTION OF THE INVENTION

This present invention relates to a novel crystalline form of ingenol mebutate. This specific crystalline form surprisingly possesses physical properties which are believed to facilitate the handling and manufacture of the API and of final dosage forms.

It is well known that the ease and safety with which dosage forms are prepared, as well as the properties of the drug, may depend on factors such as, but not limited to, the purity, solubility, homogeneity, hygroscopicity, and flow characteristics of the active pharmaceutical ingredient (API). These properties may be altered or improved if a specific crystalline, rather than an amorphous, form of the API can be produced. In accordance with the present invention, it has been surprisingly discovered that the processability and physicochemical properties of a crystalline ingenol mebutate are advantageous. For pharmaceutical formulations of the present invention, the availability of crystalline ingenol ingenol mebutate uniquely provides for a range of topical formulations using for example suspensions or micronisation or nano-processing techniques. The process for obtaining the crystalline form of the compound of formula I additionally improves purity of the compound and eliminates byproducts from the previous isolations steps.

FIG. 1 shows a characteristic FTIR-ATR spectrum of the crystalline form.

Table 1 above shows the Single Crystal Parameters for the crystalline form. Selected atomic coordinates and isotropic thermal parameters determined from the data are provided in Table 2. Bond lengths and bond angles are set forth in Table 3. Other crystal data and structure refinement details are provided in Table 4.

Formula 2 above shows the Single Crystal Configuration of crystalline ingenol mebutate.

A crystalline composition of matter disclosed herein may be prepared from amorphous (i.e. noncrystalline) or impure ingenol mebutate. The preparation of ingenol mebutate is disclosed by EP1015413 B1, or by Hohmann et. al., Planta Med. 66, 3, (2000), both of which are incorporated herein by reference in entirety.

A presently preferred method of forming crystalline ingenol mebutate comprises dissolving the amorphous compound in a solvent or solvent mixture. Presently preferred solvents include $C_1$-$C_6$ linear or branched alkyl alcohols such as ethanol and $C_2$-$C_6$ linear or branched alkyl nitriles such as acetonitrile. In an aspect of the invention the solvent is acetone, ethanol, 2-propanol, heptane, methyl tert-butyl ether, monoglyme, toluene, a mixture of acetone and heptane, a mixture of acetone and c-hexane, a mixture of acetone and i-octane, a mixture of acetone and xylene, a mixture of acetonitrile and water, a mixture of 2-propanol and water, a mixture of 2-propanol and heptane, a mixture of 1,4 dioxane and heptane, a mixture of 1,4 dioxane, dimethyl sulfoxide and heptane or a mixture of toluene and heptane.

Preferably, the solvent is heated, the amorphous compound dissolved in it to a point approximately equal to saturation, water optionally added, and the resulting solution allowed to cool to a temperature at which the full amount of the compound dissolved is no longer soluble in the solvent or solvent mixture. Crystals are isolated by filtration and dried, optionally in vacuo optionally at an elevated temperature.

In yet another aspect, this invention relates to isolated crystalline ingenol mebutate of the present invention as defined above which has a polymorphic purity of at least about 80%, such as about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In yet another aspect, this invention relates to isolated ingenol mebutate of the present invention as defined above which has a degree of crystallinity of at least about 80%, such as about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In yet another aspect, this invention relates to isolated crystalline ingenol mebutate of the present invention as defined above which contains at least about 90% of isoform 'b', i.e. ingenol-3-mebutate, such as about 90%, about about 91%, about 92%, about 93%, about 94%, about 95%, about 96%, about 97%, about 98%, about 99%, or about 100%.

Pharmaceutical Formulations and Methods of Treatment

A further embodiment of the invention encompasses pharmaceutical compositions comprising a crystalline form of a compound of Formula 1 and one or more pharmaceutically acceptable carriers or vehicles.

Pharmaceutical formulations may include topical, oral, rectal, parental (intravenous, intramuscular), transdermal, buccal, nasal, sublingual, or subcutaneous administration.

In one specific embodiment, the pharmaceutical compositions of the invention are suitable for topical administration.

The crystalline form of a compound of formula I is useful in pharmaceutical formulations wherein the compound remains as crystal such as in a suspensions.

Suspensions can be made from processed crystalline ingenol mebutate such as micronized or nano-processed crystalline ingenol mebutate. The suspension may be used as it is in for example aerosols or processed into other pharmaceutical formulations such as creams, gels, ointments or other formulations useful for topical application.

In general, the crystalline ingenol mebutate is dispersed in a vehicle. The vehicle can be water or another suitable vehicle, wherein the crystalline ingenol mebutate is maintained as a suspension and which has a viscosity suitable for delivery and for preventing the active substance in settling during storage. The vehicle may also be solvent mixtures.

Further additives may be stabilizers, emulsifiers, penetration enhancers, gelling agents and other components commonly used in dermal formulations, e.g., antioxidants, preservatives, pigments, skin soothing agents, skin healing agents and skin conditioning agents cf. *CTFA Cosmetic Ingredients Handbook*, $2^{nd}$ Ed., 1992. In one embodiment of the invention, the preservative is benzyl alcohol.

The present invention provides a suspension of crystalline ingenol mebutate for pharmaceutical purposes as described above. Concentration of compound in the pharmaceutical formulation is determined on the basis of the disease to be treated. For topical administration, a crystalline ingenol mebutate may typically be present in an amount of from about 0.001 to about 20% by weight of the composition, such as about 0.01% to about 10%. In other embodiments of the present invention, a crystalline ingenol mebutate is present in an amount of about 0.05% to about 1% by weight. In another embodiment of the present invention, a crystalline ingenol mebutate is present in an amount of about 0.01% to about 0.5%. In yet another embodiment of the present invention, a crystalline ingenol mebutate is present in a concentration of around 0.1%.

Examples of pharmaceutical formulations of the present invention include topical pharmaceutical gels formulated with, e.g., 0.015% or 0.05% ingenol mebutate (amorphous or crystallized) by weight of the gel, isopropyl alcohol, hydroxyethylcellulose, citric acid monohydrate, sodium citrate dihydrate, benzyl alcohol and purified water.

In the treatment of, for example, actinic keratosis on the face and/or scalp of a subject, a 0.015% ingenol mebutate topical gel of the present invention may be applied on the face and scalp to the affected skin area (treatment area) once a day for 3 consecutive days.

In the treatment of, for example, actinic keratosis on the trunk and/or extremities of a subject, a 0.05% ingenol mebutate topical gel of the present invention may be applied on the trunk and extremities to the affected skin area (treatment area) once a day for 2 consecutive days.

A treatment area can be defined, for example, as one contiguous area of approximately 25 cm² (e.g., 5 cm×5 cm). The gel from for example a unit dose tube or package containing approximately 0.47 g of the gel, can be squeezed onto the fingertip and spread evenly over the entire treatment area, allowing the gel to dry for about 15 minutes. Preferably, one unit dose tube (tube with screw cap or individual packets) may be used for one treatment area. Immediately following application of a gel to the treatment area, subjects should wash their hands.

Under maximum use conditions, e.g., when an about 100 cm² contiguous treatment area is topically treated with 4 unit doses of 0.05% ingenol mebutate gel once daily for 2 consecutive days, it is believed that there is little to no systemic absorption of the ingenol mebutate. Thus, it is contemplated by the present invention that up to at least about 2 unit dose tubes, each filled with 0.05% ingenol mebutate gel in an amount of about 0.47 g, or about 6 unit dose tubes, each filled with 0.015% ingenol mebutate gel in an amount of about 0.47 g, may be applied to a treatment area once daily for 2 consecutive days, that totals a maximum treatment area affected with actinic keratosis of about 100 cm², without causing treatment limiting systemic absorption of ingenol mebutate.

A further embodiment of the invention encompasses the use of a crystalline form of a compound of Formula 1 as a medicament.

In an another embodiment of the present invention, it encompasses the use of a crystalline form of a compound of formula 1 for the treatment of actinic keratosis or solar keratosis, or seborrheic keratosis.

Another embodiment of the invention encompasses a crystalline form of a compound of Formula 1 for the treatment of cancer or other conditions involving neoplastic cells, viral infections, bacterial infections, wound healing, photodamaged skin and skin wrinkles.

In an embodiment of the invention, a crystalline form of a compound of Formula 1 is contemplated for use in the treatment of basal cell carcinoma (BCC), nodular BCC, superficial basal cell carcinoma (sBCC), squamous cell carcinoma or squamous cell carcinoma in situ (SCCIS).

In an embodiment of the invention, a crystalline form of a compound of Formula 1 is contemplated for use in the treatment of actinic keratosis.

In an embodiment of the invention, a crystalline form of a compound of Formula 1 is contemplated for use in the treatment of Seborrheic keratosis.

In an embodiment of the invention, a crystalline form of a compound of Formula 1 is contemplated for use in the treatment of photodamaged skin and fine wrinkles.

In an embodiment of the invention, a crystalline form of a compound of Formula 1 is contemplated for use in the treatment of a lesion or disorder caused by HPV infection.

In an embodiment of the invention, a lesion is a common wart or a genital or peri-anal wart.

In an embodiment of the invention the use of a crystalline form of a compound of Formula 1 for the manufacture of a medicament for the treatment of actinic keratosis or solar keratosis is contemplated.

In an embodiment of the invention the use of a crystalline form of a compound of Formula 1 for the manufacture of a medicament for the treatment of seborrheic keratosis is contemplated.

In an embodiment of the invention the use of a crystalline form of a compound of Formula 1 for the manufacture of a medicament for the treatment of cancer or other conditions involving neoplastic cells is contemplated.

In an embodiment of the invention the use of a crystalline form of a compound of Formula 1 for the manufacture of a medicament for the treatment of viral infections, bacterial infections, wound healing, photodamaged skin and skin wrinkles is contemplated.

In an embodiment of the invention the use of a crystalline form of a compound of Formula 1 for the manufacture of a medicament for the treatment of basal cell carcinoma (BCC), nodular BCC, superficial basal cell carcinoma (sBCC), squamous cell carcinoma or squamous cell carcinoma in situ (SCCIS) is contemplated.

In an embodiment of the invention the use of a crystalline form of a compound of Formula 1 for the manufacture of a medicament for the treatment of photodamaged skin and fine wrinkles is contemplated.

In an embodiment of the invention the use of a crystalline form of a compound of Formula 1 for the manufacture of a medicament for the treatment of lesion or disorder caused by HPV infection is contemplated.

In an embodiment of the invention the use of a crystalline form of a compound of Formula 1 for the manufacture of a medicament for the treatment of common wart or a genital or peri-anal wart is contemplated.

The term "cancer" in the context of the present invention is intended to cover skin cancers, such as non-melanoma skin cancer, melanoma, malignant melanoma, Merkel cell carcinoma, squamous cell carcinoma, and basal cell carcinoma. Basal cell carcinomas cover superficial basal cell carcinomas as well as nodular basal cell carcinomas. Other cancer types include haematological cancers, such as myeloid cancers in particular such as acute myeloid leukemia and chronic myeloid leukemia; Cancer of the prostate and bladder including benign prostatic hyperplasia, prostatis intraepithelial carcinoma, carcinoma of the bladder, adenocarcinoma of the prostate and renal cell carcinoma. Other cancers include AIDS related cancer, acoustic neoma, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (bcc), bladder cancer, bone cancers, bowel cancer, brain stem glioma, brain and CNS cancers, breast cancer, CNS cancers, carcinoid cancers, cervical cancer, childhood brain cancers, childhood cancer, childhood soft tissue sarcoma, chondrosarcoma, choriocarcinoma, colorectal cancers, cutaneous T-Cell lymphoma, dermatof[iota]brosarcoma-protuberans, desmoplastic small round cell cancer, ductal carcinoma, endocrine cancers, endometrial cancer, ependymoma, esophageal cancer, Ewing's sarcoma, extra hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal carcinoid cancer, genitourinary cancers, germ cell cancers, gestational trophoblastic disease, glioma, gynecological cancers, hematological malignancies, head and neck cancer, hepatocellular cancer, hereditary breast cancer, histiocytosis, Hodgkin's disease, human papillomavirus, hydatidiform mole, hypercalcemia, hypopharynx cancer, intra-ocular melanoma, isle T-cell cancer, Kaposi's sarcoma, kidney cancer, Langerhan's cell histiocytosis, laryngeal cancer, leiomyosarcoma, li-fraumeni syndrome, lip cancer, liposarcoma, liver cancer, lung cancer, lymphedema, lymphoma, Hodgkin's lymphoma, non-Hodgkin's lymphoma, male breast cancer, malignant rhabdoid cancer of kidney, medulloblastoma, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-small cell lung cancer (nsclc), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral neuroectodermal cancers, pituitary cancer, polycythemia vera, prostate cancer, rare cancers and associated disorders, retinoblastoma, rhabdomyosarcoma, rothmund Thomson syndrome, salivary gland cancer, sarcoma, schwannoma, sezary syndrome, small cell lung cancer (sclc), small intestine cancer, soft tissue sarcoma, spinal cord cancers, stomach cancer, synovial sarcoma, testicular cancer, thymus cancer, thyroid cancer, transitional cell cancer (bladder), transitional cell cancer (renal-pelvis–/– ureter), trophoblastic cancer, urethral cancer, urinary system cancer, uroplakins, uterine sarcoma, uterus cancer, vaginal Cancer, vulva cancer, Waldenstrom's macroglobulinemia and Wilms' Cancer. The solid cancer which is treated using the methods of the present invention may be a primary lesion or may be the result of metastasis of a primary cancer. Furthermore, if the solid cancer is a metastasis of a primary cancer, the primary cancer may be either a primary solid cancer as described above or may be a dispersed primary cancer.

In an embodiment of the invention, "cancer" is skin cancer. In embodiments of the invention, skin cancer is non-melanoma skin cancer, malignant melanoma, Merkel cell carcinoma, squamous cell carcinoma, squamous cell carcinoma, or basal cell carcinoma such as superficial basal cell carcinomas or nodular basal cell carcinoma.

The term "photodamaged skin" in the context of the present invention is intended to cover fine lines, wrinkles and UV-ageing. UV ageing is often manifested by an increase in the epidermal thickness or epidermal atrophy and most notably by solar elastosis, the accumulation of elastin containing material just below the dermal-epidermal junction. Collagen and elastic fibres become fragmented and disorganised. At a cosmetic level this can be observed as a reddening and/or thickening of the skin resulting a lethery appearance, skin fragility and irregular pigmentation, loss of tone and elasticity, as well as wrinkling, dryness, sunspots and deep furrow formation.

The term "viral infections" in the context of the present invention is intended to cover HPV infections leading to formation of warts on the body, such as the skin, genitals and mouth. HPV refers to human papilloma virus. Other viruses are selected from adeno-, papova-, herpes- (such as simplex) varicella-zoster, Epstein-Barr-, CMV-, Pox- (such as small pox-) vaccinia-, hepatitis A-, hepatitis B-, hepatitis C-, Rhino-, polio-, rubella-, arbo-, rabies-, influenza-A and B, measles-, mumps-viruses, and HIV, HTLV I and II. In an embodiment of the invention HPV infection refers to common warts or genital warts.

The term "bacterial infections" in the context of the present invention is intended to cover prokaryotic and eukaryotic bacterial infections and Gram positive and Gram negative and Gram variable bacteria and intracellular bacteria. Examples of bacteries includes *Treponema, Borrelia, Neisseria, Legionella, Bordetella, Escherichia, Salmonella, Shigella, Klebsiella, Yersinia, Vibrio, Hemophilus, Rickettsia, Chlamydia, Mycoplasma, Staphylococcus, Streptococcus, Bacillus, Clostridium, Corynebacterium, Proprionibacterium, Mycobacterium, Ureaplasma* and *Listeria*. In particular the species: *Treponema pallidum, Borrelia Burgdorferi, Neisseria gonorrhoea, Legionella pneumophila, Bordetella pertussis, Escherichia coli, Salmonella typhi, salmonella typhimurium, Shigella dysenteriae, Klebsiella pneumoniae, Yersinia pestis, Vibrio cholerae, Hemophilus influenza, Rickettsia rickettsii, Chlamydia trachomatis, Mycoplasma pneumonia, Staphylococcus aureus, Streptococcus pneumoniae, Streptococcus pyogenes, Bacillus anthracis, Clostridium botulinum, Clostridium tetani, clostridium perfringens, Corynebacterium diphteriae, Proprionibacterium acne, Mycobacterium tuberculosis, Mycobacterium leprae* and *Listeriare monocytogenes*. Lower eukaryotic organism includes yeast and fungus such as *Pneumocystis nerinii, Candida albicans, Aspergillus, Histoplasma capsulatum, Blastomyces dermatitidis, Cryptococcus neoformans, Trichophyton* and *Microsporum*. Complex eukaryotic organism includes worms, insects, arachnids, nematodes, aemobe, *Entamoeba histolytica, Giardia lamblia, Trichonomonas vaginalis, Trypanosoma brucei gembiense, Trypanosoma cruzi, Blantidium coli, Toxoplasma gondii, Cryptosporidium* or *Leishmania*.

In the context of the present invention the term "wound healing" means: reducing or minimizing scar tissue or improving cosmesis or functional outcome in a wound and scar reduction, wherein the wound is cutaneous, chronic or for example diabetes associated, and includes cuts and lacerations, surgical incisions, punctures, graces, scratches, compression wounds, abrasions, friction wounds, chronic wounds, ulcers, thermal effect wounds, chemical wounds, wounds resulting from pathogenic infections, skin graft/transplant donor and recipient sites, immune response conditions, oral wounds, stomach or intestinal wounds, damaged cartilage or bone, amputation sides and corneal lesions.

A further embodiment of the invention encompasses a crystalline form of a compound of Formula 1 for the treatment of cancer, wherein the cancer is skin cancer such as malignant melanoma, merkel cell carcinoma, squamous cell carcinoma, or basal cell carcinoma.

The present invention will be exemplified by the following non-limiting examples.

EXAMPLES

Example 1

Preparation of Crystalline Ingenol Mebutate

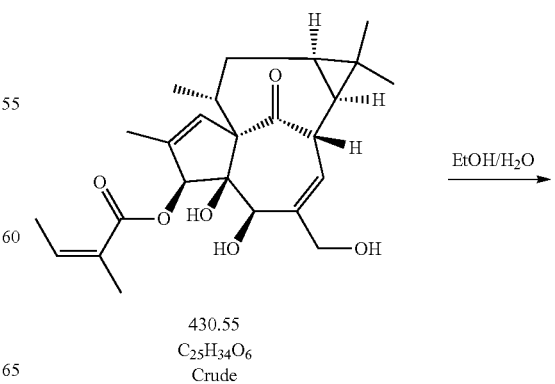

430.55
$C_{25}H_{34}O_6$
Crude

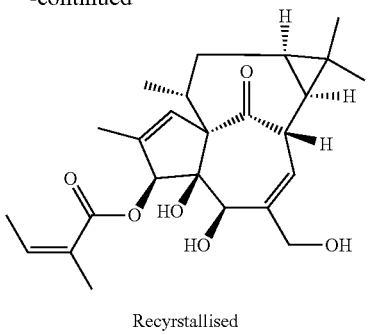

Recyrstallised

Four batches of crude Ingenol mebutate (about 22 g, 51.1 mmol) are combined in about a 500 ml vessel. Ethanol (about 154 ml) is charged to the vessel and the mixture is stirred at about 15 to 25° C. (the majority of crude ingenol mebutate was in solution after 5 minutes stirring). An oil bath is pre-heated to about 40° C. and the vessel is lowered into it (this effected full dissolution). Purified water (about 176 ml) is charged dropwise to the vessel until the mixture became permanently opaque. The mixture is stirred for about 5 to 6 minutes at about 30 to 35° C. (internal temperature), at this point the mixture is slightly opaque and a further charge of water is made (22 ml). The mixture is stirred for a further about 10 to 12 minutes at about 35 to 40° C. (internal temperature) then the heat source is removed and the opaque mixture is cooled to about 20 to 25° C. and stirred at this temperature for about 45 to 50 minutes. The reaction is further cooled to about 0 to 5° C. and stirred at this temperature for about 130 to 135 minutes. The suspension is filtered under vacuum and the collected solids are washed with half of the filtered recrystallisation liquors (used to rinse out the reaction vessel). The collected solids are further washed with purified water (2×110 ml) followed by heptane (2×110 ml) and the filter cake is dried in vacuo for about 140 minutes. The collected solids are further dried in a vacuum oven at about 40 to 45° C. to afford Ingenol mebutate as a solid (about 19.85 g, about 90% th, about 90% w/w). Purity by HPLC analysis: about 99.72 area %.

Example 2

Preparation of Crystalline Ingenol Mebutate

Five lots of crude ingenol mebutate are combined into one pool of about 43.6 g (containing about 28.07 g of ingenol mebutate) by resuspension in acetone (about 233 mL) and is transferred to a round-bottled flask that is followed by evaporation to dryness on a rotary evaporator. The dried crude ingenol mebutate pool is added to about 38 mL of acetonitrile and is then slowly rotated for about 10 minutes on the rotary evaporator while it is heated using a waterbath (about 40° C.). This results in complete dissolution after which the temperature in the water-bath is decreased by about 5° C. at about every 25-30 minutes until the temperature is left at about 25° C. for about another 25 minutes. The flask is removed from the rotary evaporator and closed prior to placing it in the freezer at about −20° C. for about 11 days. Crystals had started to grow after about 5 days. The supernatant (about 15.5 mL) is removed by the use of a Pasteur pipette before the crystals of ingenol mebutate are collected on a PTFE filter membrane using vacuum filtration. The crystallisation flask is rinsed using pre-cooled acetonitrile (24 mL) and the crystals are spread to cover the filter evenly before additional drop-wise washing using pre-cooled acetonitrile (2×24 mL) is conducted. Upon completion, the crystals are partially dried by vacuum for about 15 minutes followed by a flow of nitrogen for about 1¾ hour. This results in about 10.9 g of ingenol mebutate crystals (about 39% yield based on ingenol mebutate).

Example 3

XRC Single Crystal Structure of Crystalline Ingenol Mebutate

A representative rod-shaped crystal (about 0.3 mm×about 0.05 mm×about 0.05 mm) obtained using the method of Example 1 is surveyed and a data set is collected on a NoniusKappaCCD area detector diffractometer.

Other experimental details: Diffractometer: Nonius Kappa CCD area detector (φ scans and ω scans to fill asymmetric unit). Cell determination: DirAx (Duisenberg, A J. M. (1992). J Appl. Cryst. 25, 92-96.) Data collection: Collect (Collect: Data collection software, R Hooft, Nonius B. V., 1998). Data reduction and cell refinement: Denzo (Z. Otwinowski & W. Minor, Methods in Enzymology (1997) vol. 276: Macromolecular Crystallography part A, pp. 307-326; C. W. Carter, Jr. & R. M. Sweet, Eds., Academic Press). Absorption correction: Sheldrick, G. M. SADABS—Bruker Nonius area detector scaling and absorption correction—V2.10 Structure solution: SHELXS97 (G. M. Sheldrick, Acta Cryst. (1990) A46 467-473). Structure refinement: SHELXS97 (G. M. Sheldrick (1997), University of Göttingen, Germany). Graphics: Cameron—A Molecular Graphics Package. (D. M. Watkin, L. Pearce and C. K Prout, Chemical Crystallography Laboratory, University of Oxford, 1993).

Special Details:

All hydrogen atoms are placed in idealized positions and realigned using a riding model. There is conformational disorder in the macrocyclic ring.

Details of the crystal are provided by Table 1 above. Selected atomic coordinates and isotropic thermal parameters determined from the data are provided in Table 2. Other crystal data and structure refinement details are provided in Table 4.

TABLE 2

Atomic coordinates [×10$^4$], equivalent isotropic displacement parameters [Å$^2$ × 10$^3$] and site occupancy factors.
$U_{eq}$ is defined as one third of the trace of the orthogonalized $U^{ij}$ tensor.

| Atom. | x | y | z | $U_{eq}$ | S.o.f. |
|---|---|---|---|---|---|
| C1 | 3825(5) | 3707(5) | 428(1) | 38(1) | 1 |
| C2 | 5900(5) | 3903(5) | 425(1) | 37(1) | 1 |
| C3 | 7212(5) | 2727(5) | 453(1) | 33(1) | 1 |
| C4 | 9278(5) | 3151(6) | 417(1) | 50(1) | 1 |
| C5 | 6793(5) | 850(5) | 497(1) | 35(1) | 1 |
| C6 | 4864(6) | −1236(4) | 772(1) | 33(1) | 1 |
| C7 | 2887(6) | −1430(5) | 656(1) | 46(1) | 1 |
| C8 | 2444(8) | −1555(5) | 302(1) | 62(1) | 1 |
| C9 | 1694(6) | −1429(5) | 902(1) | 49(1) | 1 |
| C10 | 2614(5) | −1194(4) | 1225(1) | 32(1) | 1 |
| C11 | 4774(5) | −1556(4) | 1144(1) | 27(1) | 1 |
| C12A | 213(9) | 1111(9) | 1274(1) | 35(1) | 0.539(2) |
| C13A | 2274(10) | 698(9) | 1325(1) | 35(1) | 0.539(2) |
| C14A | 2828(9) | 1265(8) | 1668(1) | 35(1) | 0.539(2) |
| C15A | 1838(9) | 382(9) | 1957(1) | 35(1) | 0.539(2) |
| C16A | 2919(10) | −191(9) | 2256(2) | 35(1) | 0.539(2) |
| C17A | 2113(10) | −1546(9) | 2025(2) | 35(1) | 0.539(2) |
| C20A | 1909(10) | −75(9) | 2578(1) | 35(1) | 0.539(2) |
| C21A | 4992(9) | 65(9) | 2283(1) | 35(1) | 0.539(2) |

TABLE 2-continued

Atomic coordinates [×10⁴], equivalent isotropic displacement parameters [Å² × 10³] and site occupancy factors. $U_{eq}$ is defined as one third of the trace of the orthogonalized $U^{ij}$ tensor.

| Atom. | x | y | z | $U_{eq}$ | S.o.f. |
|---|---|---|---|---|---|
| C18A | 3229(5) | −2388(5) | 1771(1) | 35(1) | 0.539(2) |
| C12B | 1705(11) | 2107(10) | 1216(2) | 35(1) | 0.461(2) |
| C13B | 2166(12) | 586(9) | 1441(2) | 35(1) | 0.461(2) |
| C14B | 549(11) | 552(11) | 1702(2) | 35(1) | 0.461(2) |
| C15B | 606(12) | −493(10) | 2018(2) | 35(1) | 0.461(2) |
| C16B | 2124(12) | −533(11) | 2279(2) | 35(1) | 0.461(2) |
| C17B | 1868(12) | −2096(11) | 2067(2) | 35(1) | 0.461(2) |
| C20B | 1363(12) | −759(11) | 2623(2) | 35(1) | 0.461(2) |
| C21B | 3804(11) | 657(10) | 2260(2) | 35(1) | 0.461(2) |
| C18B | 3229(5) | −2388(5) | 1771(1) | 35(1) | 0.461(2) |
| C19 | 1975(5) | −2445(4) | 1474(1) | 30(1) | 1 |
| C22 | 4360(5) | −3988(4) | 1775(1) | 30(1) | 1 |
| C23 | 5375(5) | −4415(4) | 1518(1) | 26(1) | 1 |
| C24 | 5371(5) | −3501(4) | 1188(1) | 28(1) | 1 |
| C25 | 6607(5) | −5983(4) | 1526(1) | 33(1) | 1 |
| O1 | 7605(5) | −262(4) | 356(1) | 66(1) | 1 |
| O2 | 5432(4) | 550(3) | 717(1) | 30(1) | 1 |
| O3 | 6091(3) | −592(3) | 1322(1) | 28(1) | 1 |
| O4 | 587(3) | −3356(4) | 1454(1) | 41(1) | 1 |
| O5 | 7194(3) | −3705(3) | 1045(1) | 31(1) | 1 |
| O6 | 6344(4) | −7081(3) | 1249(1) | 38(1) | 1 |

TABLE 3

Bond lengths [Å]

| | |
|---|---|
| C1—C2 | 1.488(5) |
| C2—C3 | 1.311(5) |
| C3—C5 | 1.497(5) |
| C3—C4 | 1.516(5) |
| C5—O1 | 1.191(5) |
| C5—O2 | 1.350(4) |
| C6—O2 | 1.461(4) |
| C6—C7 | 1.496(6) |
| C6—C11 | 1.560(4) |
| C7—C9 | 1.327(6) |
| C7—C8 | 1.502(5) |
| C9—C10 | 1.502(5) |
| C10—C19 | 1.487(5) |
| C10—C13A | 1.543(7) |
| C10—C11 | 1.602(5) |
| C10—C13B | 1.675(8) |
| C11—O3 | 1.409(4) |
| C11—C24 | 1.578(5) |
| C12A—C13A | 1.519(10) |
| C13A—C14A | 1.539(8) |
| C14A—C15A | 1.547(9) |
| C15A—C16A | 1.524(9) |
| C15A—C17A | 1.534(9) |
| C16A—C21A | 1.496(10) |
| C16A—C20A | 1.519(9) |
| C16A—C17A | 1.532(9) |
| C17A—C18A | 1.472(7) |
| C18A—C22 | 1.480(5) |
| C18A—C19 | 1.519(4) |
| C12B—C13B | 1.538(10) |
| C13B—C14B | 1.580(10) |
| C14B—C15B | 1.539(10) |
| C15B—C16B | 1.530(11) |
| C15B—C17B | 1.548(11) |
| C16B—C17B | 1.509(11) |
| C16B—C21B | 1.514(11) |
| C16B—C20B | 1.533(10) |
| C19—O4 | 1.219(4) |
| C22—C23 | 1.329(5) |
| C23—C25 | 1.500(5) |
| C23—C24 | 1.538(4) |
| C24—O5 | 1.436(4) |
| C25—O6 | 1.440(4) |

TABLE 3-continued

Bond angles [°]

| | |
|---|---|
| C3—C2—C1 | 129.6(4) |
| C2—C3—C5 | 123.0(3) |
| C2—C3—C4 | 122.2(4) |
| C5—C3—C4 | 114.6(3) |
| O1—C5—O2 | 123.7(3) |
| O1—C5—C3 | 123.3(3) |
| O2—C5—C3 | 113.1(3) |
| O2—C6—C7 | 107.8(3) |
| O2—C6—C11 | 108.5(2) |
| C7—C6—C11 | 105.2(3) |
| C9—C7—C6 | 110.9(3) |
| C9—C7—C8 | 127.9(4) |
| C6—C7—C8 | 121.2(4) |
| C7—C9—C10 | 113.9(3) |
| C19—C10—C9 | 113.9(3) |
| C19—C10—C13A | 112.8(3) |
| C9—C10—C13A | 106.6(3) |
| C19—C10—C11 | 109.0(3) |
| C9—C10—C11 | 102.1(3) |
| C13A—C10—C11 | 112.0(4) |
| C19—C10—C13B | 96.3(3) |
| C9—C10—C13B | 119.5(4) |
| C11—C10—C13B | 116.1(4) |
| O3—C11—C6 | 113.8(3) |
| O3—C11—C24 | 105.5(2) |
| C6—C11—C24 | 104.8(2) |
| O3—C11—C10 | 115.9(3) |
| C6—C11—C10 | 102.7(3) |
| C24—C11—C10 | 113.8(3) |
| C12A—C13A—C14A | 108.4(5) |
| C12A—C13A—C10 | 108.4(5) |
| C14A—C13A—C10 | 118.6(5) |
| C13A—C14A—C15A | 118.0(5) |
| C16A—C15A—C17A | 60.1(4) |
| C16A—C15A—C14A | 121.7(6) |
| C17A—C15A—C14A | 121.0(6) |
| C21A—C16A—C20A | 113.2(5) |
| C21A—C16A—C15A | 121.5(6) |
| C20A—C16A—C15A | 117.1(6) |
| C21A—C16A—C17A | 120.6(6) |
| C20A—C16A—C17A | 114.2(6) |
| C15A—C16A—C17A | 60.3(4) |
| C18A—C17A—C16A | 123.2(6) |
| C18A—C17A—C15A | 111.8(5) |
| C16A—C17A—C15A | 59.6(4) |
| C17A—C18A—C22 | 131.2(4) |
| C17A—C18A—C19 | 105.7(4) |
| C22—C18A—C19 | 107.8(3) |
| C12B—C13B—C14B | 105.7(6) |
| C12B—C13B—C10 | 110.5(5) |
| C14B—C13B—C10 | 119.3(6) |
| C15B—C14B—C13B | 124.7(7) |
| C16B—C15B—C14B | 129.0(7) |
| C16B—C15B—C17B | 58.7(5) |
| C14B—C15B—C17B | 123.3(6) |
| C17B—C16B—C21B | 123.6(7) |
| C17B—C16B—C15B | 61.2(5) |
| C21B—C16B—C15B | 120.6(6) |
| C17B—C16B—C20B | 114.0(7) |
| C21B—C16B—C20B | 113.6(6) |
| C15B—C16B—C20B | 114.1(7) |
| C16B—C17B—C15B | 60.0(5) |
| O4—C19—C10 | 125.3(3) |
| O4—C19—C18A | 123.5(3) |
| C10—C19—C18A | 111.2(3) |
| C23—C22—C18A | 119.8(3) |
| C22—C23—C25 | 120.2(3) |
| C22—C23—C24 | 126.5(3) |
| C25—C23—C24 | 113.2(3) |
| O5—C24—C23 | 108.2(3) |
| O5—C24—C11 | 107.6(3) |
| C23—C24—C11 | 123.0(3) |
| O6—C25—C23 | 112.7(3) |
| C5—O2—C6 | 117.9(3) |

TABLE 4

Crystal data and structure refinement details

| | | |
|---|---|---|
| Identification code | 2007com0757 | (PEP005 batch 0314) |
| Empirical formula | $C_{25}H_{34}O_6$ | |
| Formula weight | 430.52 | |
| Temperature | 120(2)K | |
| Wavelength | 0.71073 Å | |
| Crystal system | Orthorhombic | |
| Space group | $P2_12_12_1$ | |
| Unit cell dimensions | a = 7.1295(4) Å | |
| | b = 7.7558(4) Å | |
| | c = 41.375(2) Å | |
| Volume | 2287.9(2) Å$^3$ | |
| Z | 4 | |
| Density (calculated) | 1.250 Mg/m$^3$ | |
| Absorption coefficient | 0.088 mm$^{-1}$ | |
| F(000) | 928 | |
| Crystal | Rod; Colourless | |
| Crystal size | 0.3 × 0.05 × 0.05 mm$^3$ | |
| θ range for data collection | 2.95-27.47° | |
| Index ranges | −5 ≤ h ≤ 9, −10 ≤ k ≤ 8, −49 ≤ l ≤ 53 | |
| Reflections collected | 13412 | |
| Independent reflections | 2943 [$R_{int}$ = 0.0467] | |
| Completeness to θ = 27.47° | 96.6% | |
| Absorption correction | Semi-empirical from equivalents | |
| Max. and min. transmission | 0.9956 and 0.9641 | |
| Refinement method | Full-matrix least-squares on F$^2$ | |
| Data/restraints/parameters | 2943/8/269 | |
| Goodness-of-fit on F$^2$ | 1.034 | |
| Final R indices [F$^2$ > 2σ(F$^2$)] | R1 = 0.0679, wR2 = 0.1439 | |
| R indices (all data) | R1 = 0.0855, wR2 = 0.1577 | |
| Largest diff. peak and hole | 0.307 and −0.392 e Å$^{-3}$ | |

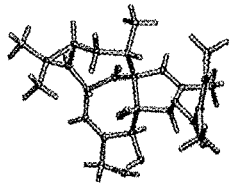

Diffractometer: Nonius KappaCCD area detector (ø scans and φ scans to fill asymmetric unit).
Cell determination: DirAx (Duisenberg, A. J. M.(1992). *J. Appl. Cryst.* 25, 92-96.)
Data collection: Collect (Collect: Data collection software, R. Hooft, Nonius B. V., 1998).
Data reduction and cell refinement: Denzo (Z. Otwinowski & W. Minor, *Methods in Enzymology* (1997) Vol. 276: *Macromolecular Crystallography*, part A, pp. 307-326;
C. W. Carter, Jr. & R. M. Sweet, Eds., Academic Press). Absorption correction: Sheldrick, G. M. SADABS - Bruker Nonius area detector scaling and absorption correction - V2.10 Structure solution: SHELXS97 (G. M. Sheldrick, *Acta Cryst.* (1990) A46 467-473).
Structure refinement: SHELXL97 (G. M. Sheldrick (1997), University of Gottingen, Germany).
Graphics: Cameron - A. Molecular Graphics Package. (D. M. Watkin, L. Pearce and C. K. Prout, Chemical Crystallography Laboratory, University of Oxford, 1993).
Special details: All hydrogen atoms were placed in idealised positions and refined using a riding model. There is confomational disorder in the macrocyclic ring.

The invention claimed is:

1. A process for preparing crystalline ingenol mebutate, which comprises (a) dissolving an amount of ingenol mebutate in a solvent or solvent mixture, (b) optionally adding water, (c) cooling the solution to a temperature at which about the full amount of ingenol mebutate is no longer soluble in the solution, and (d) isolating by filtration any ingenol mebutate crystals that are formed, wherein the crystalline ingenol mebutate is characterized by an FTIR-ATR spectrum exhibiting attenuated total reflectance peaks at approximately 3535, 2951, 1712, 1456, 1378, 1246, 1133, 1028 and 956 cm$^{-1}$ (±3 cm$^1$).

2. The process of claim 1 wherein the solvent is selected from $C_1$-$C_6$ linear or branched alkyl alcohols and $C_2$-$C_6$ linear or branched alkyl nitriles.

3. The process of claim 1, wherein the crystalline ingenol mebutate is not a solvate.

4. The process of claim 1, wherein the crystalline ingenol mebutate is orthorhombic.

5. The process of claim 1, wherein the crystalline ingenol mebutate belongs to the space group $P2_12_12_1$.

6. The process of claim 1, wherein the crystalline ingenol mebutate has a differential scanning calorimetry curve comprising an event with an onset at about 153±5° C.

7. The process of claim 1, wherein the crystalline ingenol mebutate has XRC single crystal parameters that are substantially identical to those provided in Table 1.

8. The process of claim 1, wherein the crystalline ingenol mebutate comprises (a) atoms at atomic positions relative to the origin of the unit cell as set forth in Table 2, or (b) bond lengths or bond angles as set forth in Table 3.

9. The process of claim 1, wherein the crystalline ingenol mebutate has a XRC single crystal structure according to Formula 2.

10. The process of claim 1, wherein the crystalline ingenol mebutate has a purity of at least about 99.5%.

11. The process of claim 1, wherein the crystalline ingenol mebutate has a purity of at least about 99.7%.

12. The process of claim 1, wherein the crystalline ingenol mebutate has a purity of at least about 99.9%.

13. The process of claim 1, wherein the solvent or solvent mixture comprises a $C_1$-$C_6$ linear or branched alkyl alcohol.

14. The process of claim 13, wherein the $C_1$-$C_6$ linear or branched alkyl alcohol is ethanol.

15. The process of claim 1, wherein the solvent or solvent mixture comprises a $C_2$-$C_6$ linear or branched alkyl nitrile.

16. The process of claim 15, wherein the $C_2$-$C_6$ linear or branched alkyl nitrile is acetonitrile.

* * * * *